United States Patent [19]

Eberle

[11] Patent Number: 5,183,048
[45] Date of Patent: Feb. 2, 1993

[54] METHOD AND APPARATUS FOR REMOVING ARTIFACTS FROM AN ULTRASONICALLY GENERATED IMAGE OF A SMALL CAVITY

[75] Inventor: Michael J. Eberle, Lobata, Calif.

[73] Assignee: Endosonics Corporation, Rancho Cordova, Calif.

[21] Appl. No.: 719,804

[22] Filed: Jun. 24, 1991

[51] Int. Cl.$^5$ .............................................. A61B 8/12
[52] U.S. Cl. ........................... 128/662.06; 128/661.01
[58] Field of Search ....................... 128/660.01, 661.07, 128/662.06; 73/618, 625, 626

[56] References Cited

U.S. PATENT DOCUMENTS

| | | | |
|---|---|---|---|
| 3,827,115 | 8/1974 | Bom | 128/662.06 |
| 3,938,502 | 2/1976 | Bom | 128/662.06 |
| 4,127,034 | 11/1978 | Lederman et al. | 73/626 |
| 4,325,257 | 4/1982 | Kino et al. | 73/626 |
| 4,386,339 | 5/1983 | Henry et al. | 307/361 |
| 4,505,156 | 3/1985 | Questo | 73/626 |
| 4,509,524 | 4/1985 | Miwa | 128/660.07 X |
| 4,576,177 | 3/1986 | Webster, Jr. | 128/662.06 |
| 4,641,657 | 2/1987 | Ellis | 128/630 |
| 4,671,293 | 6/1987 | Shaulov | 128/662.03 |
| 4,917,097 | 4/1990 | Proudion et al. | 128/662.06 |
| 4,977,655 | 12/1990 | Martinelli | 128/662.06 X |

OTHER PUBLICATIONS

Black, William C., Jr., "High Speed CMOS A/D Conversion Techniques," University of California, Berkeley, Electronics Research laboratory, Mem. No. UCB-/ERL M80/54, Nov. 1980, pp. 180-243.
Black, William C., Jr., "Time Interleaved Converter Arrays," IEEE Journal of Solid-State Circuits, vol. SC-15, No. 6, Dec. 1980, pp. 1022-1029.
Corcoran et al., "A 1GHz 6b ADC System," Proceedings of IEEE International Solid-State Circuits Conference; IEEE 1987, pp. 102-103, 359-360.
Corcoran et al., "A 400 Mhz 6b ADC," Proceedings of IEEE International Solid-State Circuits Conference; IEEE 1987, pp. 294-297, 357.
S. J. Norton, "Reconstruction of A Reflectivity Field from Line Integrals Over Circular Paths," J. Acous. Soc. Am. vol. 67 #3, pp. 853-863, Mar. 1980.
A. Macovski, "Ultrasonic Imaging Using Arrays," Proc. IEEE, vol. 67 #4, pp. 484-495, Apr. 1979.
Benett, Peterson, Corl & Kino, "A Real-Time Synthetic Aperture Digital Acoustic Imaging System," Acoustical Imaging, vol. 10, pp. 669-692, Plenum Press, N.Y., 1982.
Mersereau and Oppenheim, "Digital Reconstruction of Multidimensional Signals From Their Projections," IEEE, vol. 62, No. 10, pp. 1319-1338, Oct. 1974.
R. W. Schafer and L. R. Rabiner, "A Digital Signal Processing Approach To Interpolation," IEEE, vol. 61, No. 6, Jun. 1973, pp. 692-702.
M. H. Lee, J. H. Kim & S. B. Park, "Analysis of A Scan Conversion Algorithm For A Real-Time Sector Scanner", IEEE, vol. M1-5, No. 2, Jun. 1986, pp. 96-105.
R. W. Martin et al., "Signal Enhancement for Automatic Identification of Arterial Wall Echos From An Intravessel Scanner", *Ultrasound In Medicine*, vol. 4, (New York, 1978), pp. 417-431.

*Primary Examiner*—Francis Jaworski
*Attorney, Agent, or Firm*—Leydig, Voit & Mayer

[57] ABSTRACT

An apparatus and method for imaging a small cavity is disclosed wherein reference waveforms to be used in obtaining an improved image are generated in vivo instead of in vitro as is the conventional procedure. The reference waveforms are used to strip the imaging signals of noise that otherwise produces artifacts in an image generated from the signals. The imaging probe is first inserted into a first area of the vascular system to be imaged and reference waveforms are collected. After collecting the reference waveforms, the imaging probe is further inserted into the vascular system to a second area that is to be imaged. If new reference waveforms are required, the imaging probe is simply withdrawn to the first area of the vascular system wherein new reference waveforms are collected, and then the imaging probe is again further inserted to the second area, which then is imaged. The present invention also provides an imaging apparatus capable of imaging close to the surface of the probe and, in this regard, removes artifacts in the imaging waveforms that usually form a corona in the visual image about the perimeter of the probe.

12 Claims, 7 Drawing Sheets

METHOD AND APPARATUS FOR REMOVING ARTIFACTS FROM AN ULTRASONICALLY GENERATED IMAGE OF A SMALL CAVITY

FIELD OF THE INVENTION

The present invention relates generally to an ultrasonic imaging apparatus for imaging small cavities such as coronary arteries, and more particularly to a method and apparatus for removing artifacts from a generated image.

BACKGROUND OF THE INVENTION

Percutaneous transluminal coronary angioplasty (PTCA) provides an alternative to coronary artery bypass graphs or open-heart surgery as means for treating atherosclerosis. Atherosclerosis is a particular type of heart disease wherein the deposition of fatty material on the inside of vessel walls throughout the body causes the artery to narrow and restrict the flow of blood. If the artery becomes too narrow, the heart muscle that is nourished by the artery receives insufficient oxygen and a myocardial infarction or heart attack can occur. Atherosclerosis can occur throughout the human body, however, it is most life threatening within the coronary vasculature.

Transluminal angioplasty surgery utilizes an elongated, flexible catheter having an inflatable balloon at its distal end that is inserted at an appropriate position into the vascular system of a patient. After the catheter is inserted into the vascular system, its balloon is routed to a stenosis. Once the balloon is properly positioned relative to the stenotic lesion, it is inflated with fluid under relatively high pressure. As the balloon expands, it dilates the stenosis, thus allowing blood to flow more freely.

Ultrasonic imaging devices have been developed for imaging inner walls or inner peripheral features of a blood vessel so as to determine the location of a stenotic lesion or stenosis and to obtain a visual image of the stenosis for diagnosis purposes. An example of such an ultrasonic imaging device is disclosed in U.S. Pat. No. 4,917,097 issued to Proudian et al., which is hereby incorporated by reference.

Ultrasonic imaging devices such as the one illustrated in the '097 patent to Proudian et al. include piezoelectric elements or transducers for generating ultrasonic waves and detecting echoes or reflections off the inner wall of the stenotic lesion. The piezoelectric elements flex in response to a received electric pulse and generate an ultrasonic wave in response to the electrically-induced flexing. Mechanical relaxation of a piezoelectric element after it has been electrically excited results in a damped oscillation of the transducer element, which causes the element to generate an electrical signal typically referred to as a "ringdown" signal.

Initially, the ringdown signal generated by the piezoelectric element is generally a much stronger signal than the signal typically generated by an echo of the ultrasonic wave. In fact, the ringdown signal can be as much as 80 decibels (dB) larger than the echo signal. Because the ringdown signal is so large relative to the echo signal, the amplitude of the ringdown signal is enough to saturate the front-end amplifiers of the imaging device circuitry and thus create artifacts in the image. This saturation of the amplifiers effectively creates a blind spot or corona in the generated image corresponding to an area immediately adjacent to the surface of the transducers.

Interference with the echo signal by the ringdown signal has resulted in various attempts to solve the problem. One current method of removing the ringdown signal is to store a reference waveform that corresponds to the ringdown signal and other factors, such as the ambient environment, that create a characteristic damped mechanical oscillation pattern of each transducer when flexed in response to an electrical pulse. This characteristic reference waveform is stored and then later subtracted from received echo signals. Since a received echo signal includes both the reflected ultrasonic wave signal and the reference signal, subtracting the stored reference signal from the total received echo signal, or real-time signal, will theoretically leave only the reflected ultrasonic wave signal or imaging signal. This technique is effective in the region of the ringdown signal within a linear region of amplification; however, it is not effective in the region of the signal that is clipped by a saturated amplifier. Because the ringdown signal is initially so much greater in amplitude than the echo signal, the first part of the ringdown signal typically saturates the amplifiers of the imaging device at its highest amplitudes.

In order to obtain an accurate reference waveform corresponding to the ringdown signal, the imaging apparatus must be in an echo-free environment so that the received and stored signal is composed of only the reference waveform and not any reflections off the inner wall of the vascular system. The transducers of the imaging probe, which transmit the pulse signals and receive the echo signals, must perceive the same acoustic impedance during the collection of a reference waveform and during the collection of an echo signal so the reference signal is matched in phase and amplitude with the ringdown signal generated while imaging the blood vessel.

One technique for obtaining a reference waveform is to place the imaging device within a large water-filled tank before the catheter is inserted into the body of the patient. This technique makes it difficult to match the acoustic impedance of the water with that of the blood in the vascular system. Therefore, the amplitude and phase of the ringdown signal generated and recorded in the environment of the water-filled tank may be somewhat different than the ringdown signal generated in the blood. Another problem associated with this technique is drifting of the ringdown signal caused by variations in temperature between the water in the tank and the blood in the vascular system. Moreover, sterility of the catheter may also be compromised by placing the sterile catheter in a tank of water or saline solution prior to insertion into a patient.

OBJECTS AND SUMMARY OF THE INVENTION

In view of the foregoing, it is a primary object of the present invention to provide an improved method for imaging a blood vessel by collecting all reference and imaging data in vivo, thereby eliminating in vitro collection of reference data and any associated risk of contamination.

It is also an object of the present invention to simplify the imaging procedure and to reduce the time required to prepare the imaging apparatus for surgery by eliminating the external reference collection procedure.

Another object of the present invention is to improve the generated image by more closely matching the phase and amplitudes of the reference waveform with that of the ringdown signal generated during the imaging process.

A further object of the invention is to provide an improved imaging apparatus that is capable of imaging smaller coronary vessels than was previous possible.

Briefly, data for a reference waveform is collected for only a portion of the sampling time period usually dedicated to detecting an entire echo waveform. By collecting reference data for only a portion of the total sampling time period, the reference data can be collected in a smaller echo-free environment than previously possible. In this regard, the reference data is collected over a portion of the sampling time period that is small enough so the data can be collected in one of the larger areas of the vascular system. In a normal PTCA procedure, the probe is inserted into an area of the vascular system having a characteristic radius that is sufficient for an entire set of reference data to be collected without the presence of an echo.

The portion of the total sampling time period used to record the reference signal corresponds approximately to the time period necessary for the damped mechanical oscillating of a transducer element to substantially subside. In this regard, the imaging probe is initially inserted into a first area of a vascular system having a radius large enough to enable the damped mechanical oscillating of an imaging transducer to substantially subside before an echo impinges on the transducer. The electrical signal generated by the damped oscillation of the transducer is stored as a reference waveform to be subtracted from subsequently acquired echo waveforms.

In the illustrated embodiment, the echo waveform is collected over 2048 sample points spaced at a predetermined interval. The reference waveform is also composed of 2048 sample points at the same predetermined interval. In collecting the reference waveform, however, it may be that only the first 500-600 sample points are filled with values of the signal generated by the transducer, depending on the decay rate of the oscillation by the transducer. The remaining sample points are filled with zero. By reducing the data points required for the reference waveform to 500-600, the reference waveform no longer must be gathered in vitro.

After collecting reference waveforms for each transducer element, the imaging probe is inserted into the area of the vascular system to be imaged. If new reference waveforms are required, the imaging probe is simply drawn back to the first area of the vascular system and reference waveforms are collected again. The imaging probe is then again inserted to the second area for imaging.

In prior art devices, the reference waveform is stored after it has been amplified by a chain of amplifiers intended for amplifying the small signals generated by a typical echo impinging on a transducer. The high gain amplification of the electrical "ringdown" signal generated as the transducer oscillates after it has been excited results in the saturation of the amplifiers and the clipping of the output signal. The clipping of the ringdown signal causes loss of any echo signal that may be impressed on it. Therefore, the probe typically has a blind spot in the immediate near field of the transducer.

In order to remove the blind spot, the reduced set of data points comprising the reference waveform may be collected at a pre-amplification stage where no clipping has yet occurred. With a stored reference waveform, the ringdown signal can be subtracted from an echo waveform at the same pre-amplification stage in order to leave an echo waveform that includes echo information in the near field that was previously lost due to clipping of the imaging signal.

Other objects and advantages of the present invention will become apparent upon consideration of the following detailed description when taken in conjunction with the drawings.

BRIEF DESCRIPTION OF THE DRAWINGS

FIG. 2b is an enlarged view of the imaging probe shown in FIG. 2a;

While the invention will be described in connection with angioplasty or PTCA surgery, it should be understood that it is not intended to be limited to such use. On the contrary, the invention is intended to cover all applications which may require imaging in a small cavity. An example of such an alternative application is the use of the invention on the end of a catheter without the incorporation of a balloon. A specific example of such a use is a pharmaceutically therapeutic use where cholesterol-inhibiting drugs are used for regional therapy and the imaging device of the invention is used to monitor the effectiveness of the drugs in removing plaque. Another specific example of an alternative use is a physical therapeutic use such as measuring blood flow rates (using Doppler sound imaging in conjunction with the invention) or determining sizes and locations of gall stones and the like. Yet another example of an alternative application is the incorporation of the invention into a catheter in conjunction with a laser or similar device for burning plaque in the arteries.

Furthermore, for the imaging device of the present invention, an ambient environment of blood is considered to be free of acoustic echoes. As will be appreciated by those skilled in the art of ultrasonic imaging, blood may generate weak echo signals whose precise characteristics depend on the nature of the imaging device employed—e.g., the frequency of the ultrasonic wave. In the imaging device employed by the present invention, which is more fully described in the Proudian et al. patent, the echoes from blood are very weak, and an ambient environment of blood in effect is free of echoes.

DETAILED DESCRIPTION OF THE PREFERRED EMBODIMENTS

Figure 1:
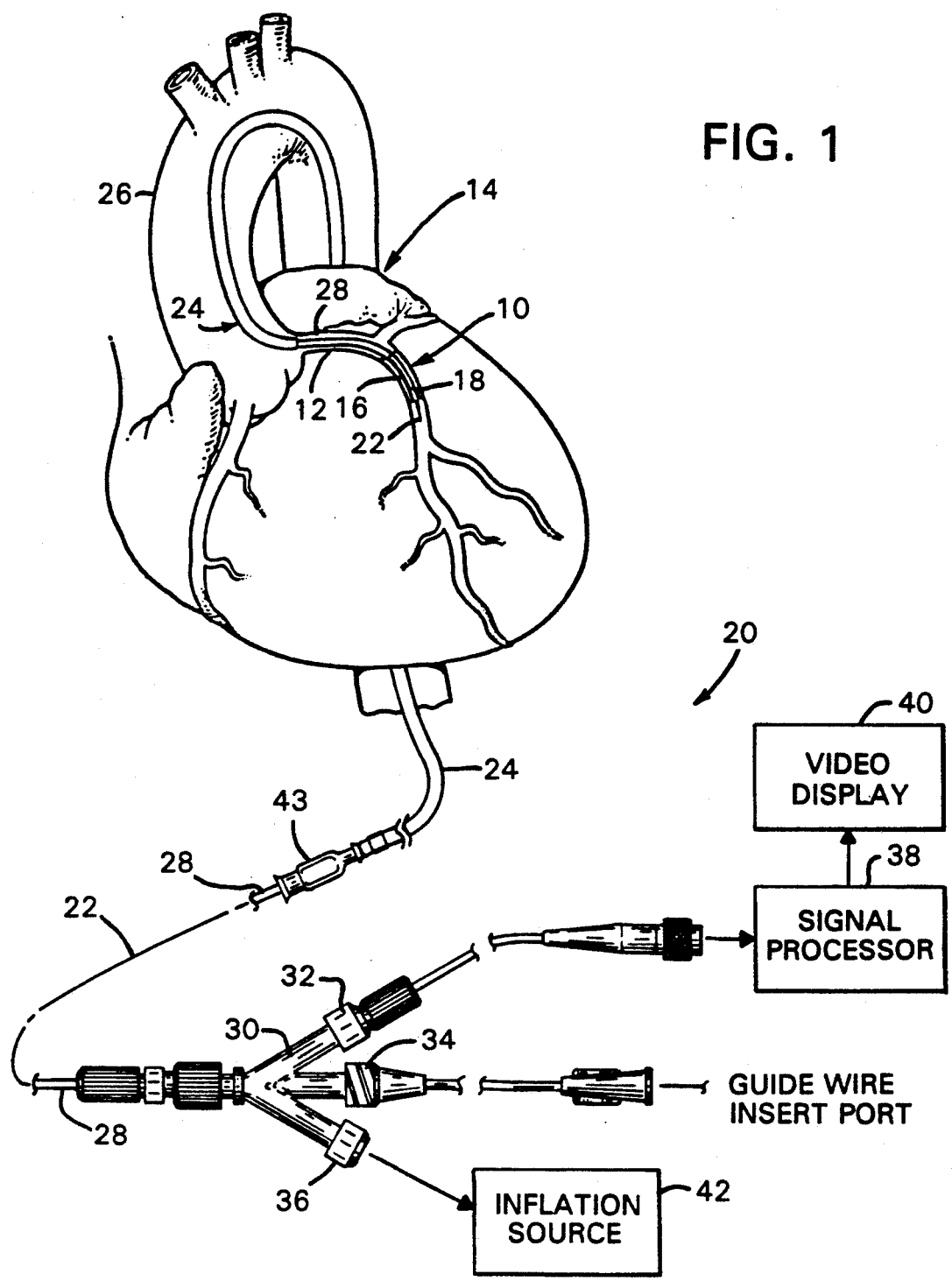
FIG. 1 is a system-type diagram of an ultrasonic imaging apparatus of the present invention illustrating the use of the apparatus to image a coronary artery during a PTCA procedure.

Turning to the drawings and referring first to FIG. 1, a dilating and imaging apparatus 10 is illustrated in a coronary artery 12 of a heart 14. The coronary artery 12 contains a buildup of fatty material or plaque 16 causing the coronary artery 12 to become occluded or have a stenosis.

As is well known in the art, the occluded section or stenosis 16 of the artery 12 is treated by inserting a balloon 18 of the dilating apparatus 10, in a low profile or deflated state, into the artery 12 using a catheter assembly 20. As shown in FIG. 1, the catheter assembly 20 includes a three-part assembly, having a guide wire 22, a guide catheter 24 for threading through large arteries such as the aorta 26, and a small diameter catheter 28 that fits inside the guide catheter 24. The catheter assembly 20 includes a tri-arm adapter 30 having a signal processor port 32, a guide wire insert port 34, and an inflation port 36 that is in communication with a fluid lumen in the catheter 28. The tri-arm adapter 30 enables a signal processor 38 that is linked to a video display 40, a guide wire 22, and an inflation source 42 all to be interconnected within the smaller catheter 28 and to communicate with the dilating and imaging apparatus 10. The smaller catheter 28 is inserted into the larger guide catheter 24 by means of a lure lock connector or angioplasty manifold 43 for entering the heart 14. The smaller diameter catheter 28 and the larger diameter catheter 24 may be made of a suitable, flexible material such as polyolefin or polyvinylchloride.

After a surgeon directs the guide wire 22 and then the guide catheter 24 through a large artery leading into the aorta 26, the smaller diameter catheter 28 is inserted. At the beginning of the coronary artery 26 that is partially occluded by the stenosis 16, the guide wire 22 is first extended into the artery 12, followed by the smaller catheter 28, which includes the balloon 18 on a distal end of the catheter 28.

The imaging probe 44 secured to a distal end of the catheter 28 provides an image on the visual display 40 that indicates when the balloon 18 is within a partially blocked area, such as the stenosis 16, of the artery 12. After locating the partially blocked area, the tip of the catheter 28 including the imaging probe 44 is moved past the blocked area in order to bring the balloon 18 into the blocked area. The balloon 18 is then inflated so as to expand the stenotic lesion 16 causing the blockage. The cardiologist may check the results of the PTCA procedure by slightly withdrawing the catheter 28 in order to bring the imaging probe 44 back into the blocked stenosis 16 so that the imaging probe 44 may image the stenosis 16. If the PTCA procedure was successful, the image on the video display 40 will show that the flow passage of the artery 12 has increased in diameter.

Figure 2A:
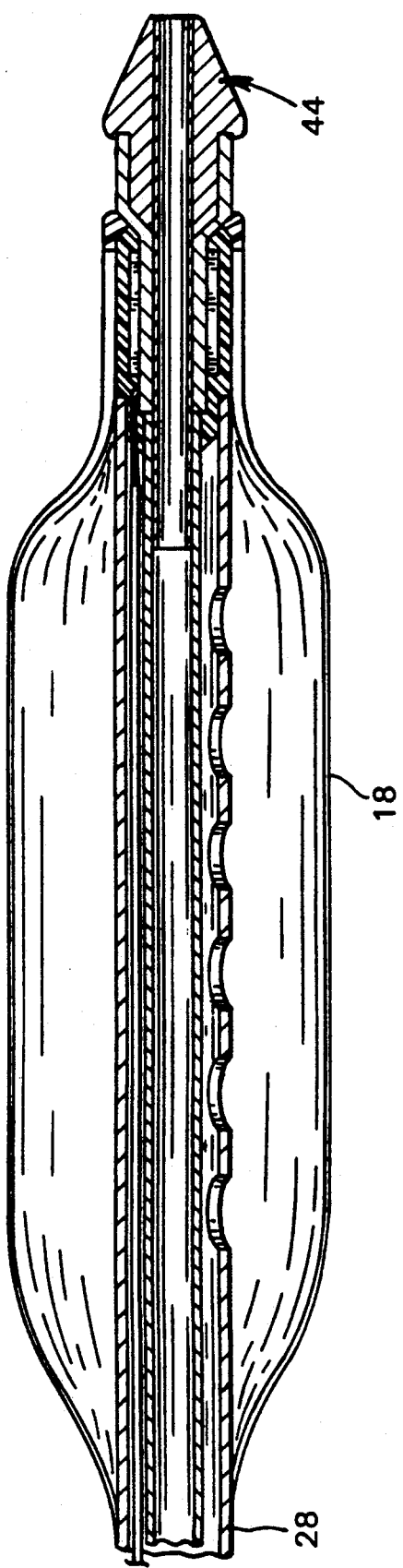
FIG. 2a is an enlarged cross-sectional view of one embodiment of the probe of the imaging apparatus at the distal end of an inflatable balloon on a catheter taken along a longitudinal axis of the catheter.
Figure 2B:
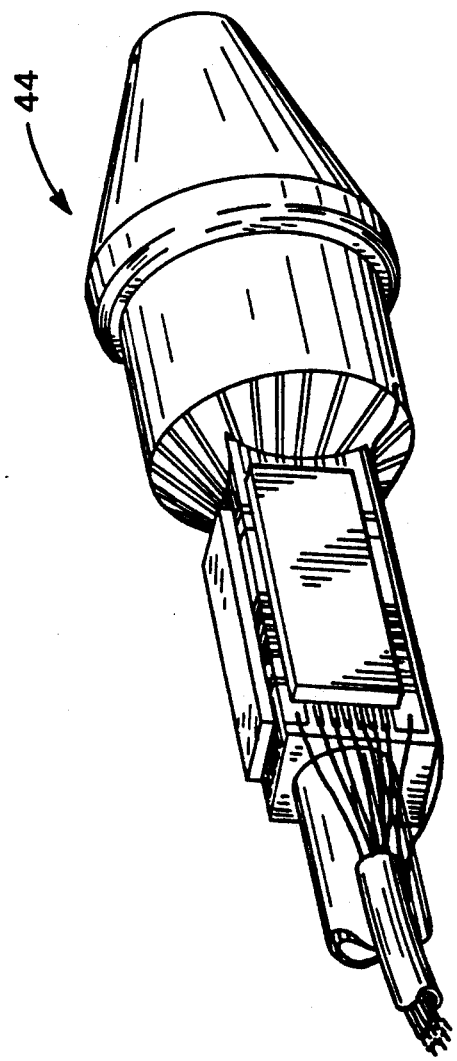

FIG. 2a is an enlarged cross-sectional view of a distal end of one embodiment of the dilating balloon 18 and imaging probe 44 taken along a longitudinal axis of the catheter 28, and FIG. 2b is an enlarged view of the imaging probe 44 shown in FIG. 2a that illustrates the imaging probe 44 positioned on the extreme distal end of the catheter 28. Details of the imaging probe 44 and its circuitry can be obtained from the previously mentioned U.S. Pat. No. 4,917,097 to Proudian et al. Additional details concerning the probe 44 and its positioning on the catheter 28 with respect to the balloon 18 can be found in U.S. application Ser. No. 07/638,192.

Figure 3A:
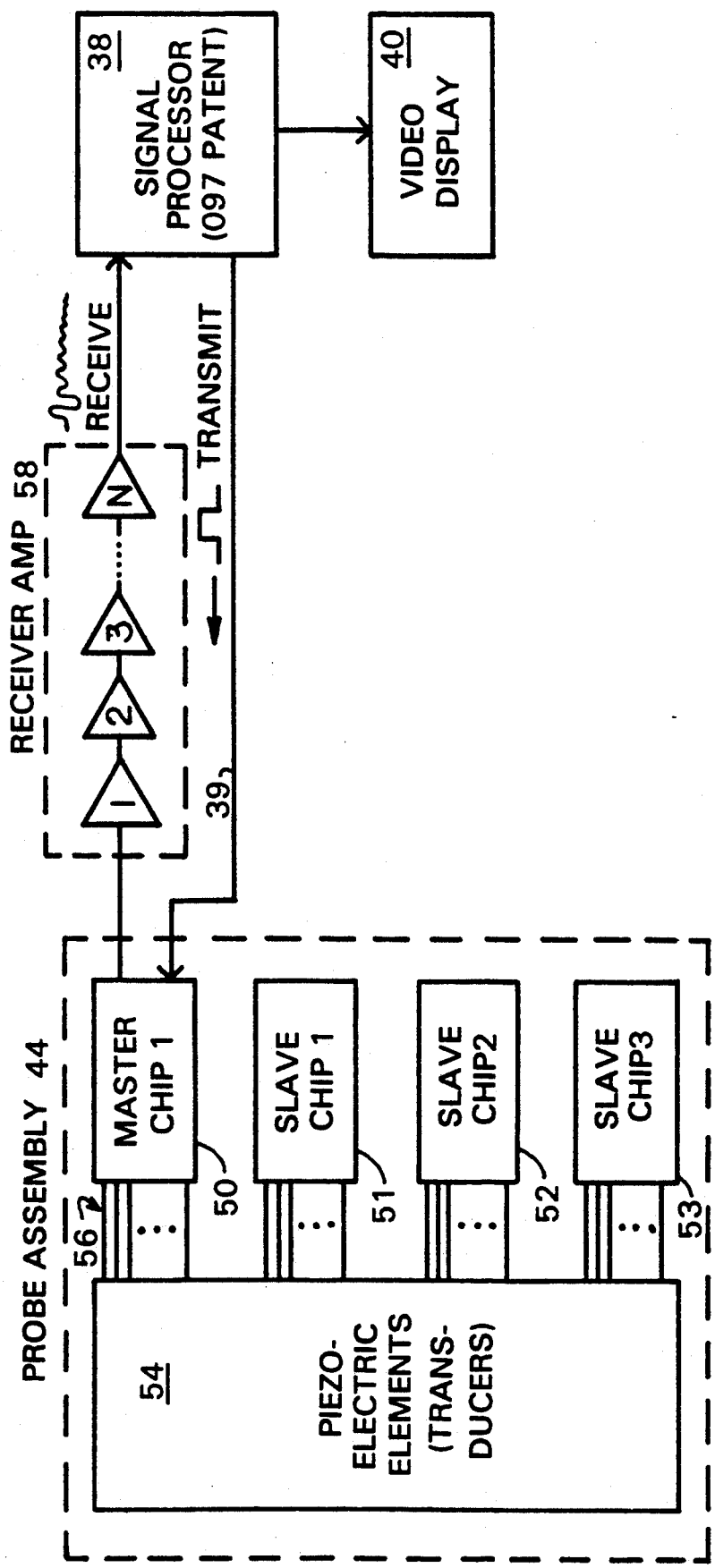
FIG. 3a is a schematic of a prior art imaging system responsive to the imaging probe and including a chain of amplifiers for amplifying the electrical signals generated by the probe.
Figure 3B:
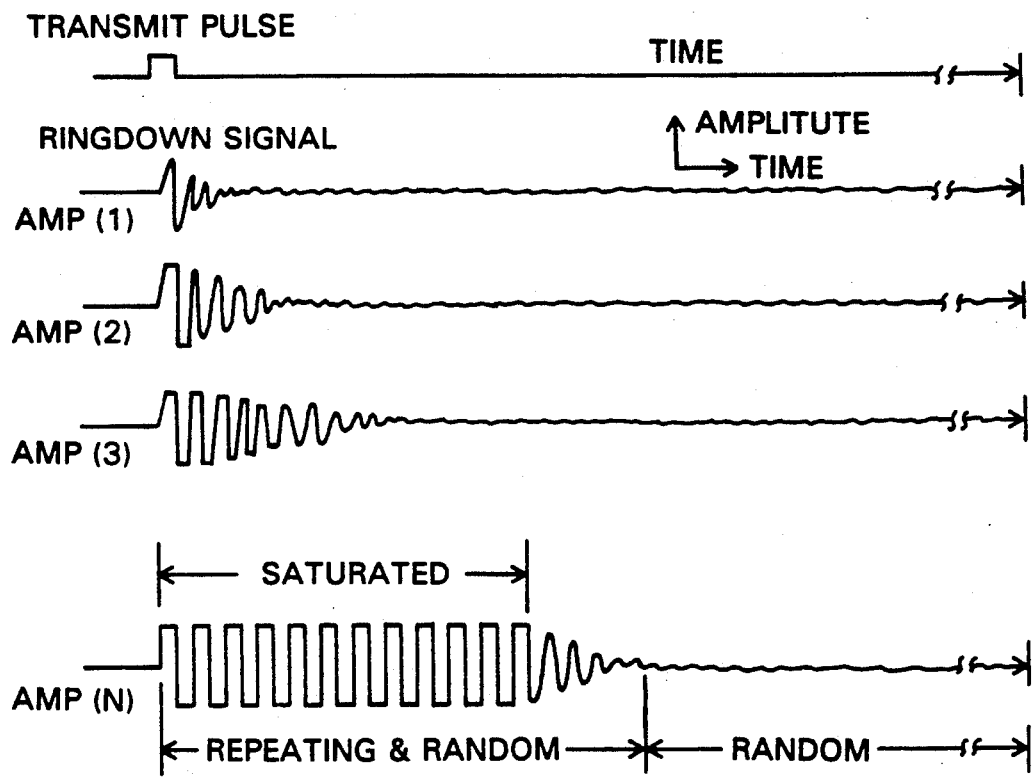
FIG. 3b illustrates a waveform generated by electrical signals from the probe, as it is amplified by the chain of amplifiers in the imaging system of FIG. 3a such that a portion of a ringdown signal in the waveform is clipped.

FIG. 3a is a schematic of an imaging system utilized in imaging devices for small cavities, and FIG. 3b illustrates a series of waveforms showing a ringdown signal being amplified to a point of saturation. Referring first to FIG. 3a, the signal processor 38 transmits an excitation pulse via line 39 to a master chip 50 which in turn cooperates with three slave chips 51,52,53 to distribute excitation pulses to each element in an array of piezoelectric elements or transducers 54 of the probe 44. Each of the chips 50-53 is electronically connected to a group of the piezoelectric elements 54 via lines 56. A detailed explanation of the chips 50-53, piezoelectric elements 54 and the interaction between the two can be found in the aforementioned Proudian et al. patent.

Each transducer or element of the array 54 responds to a received pulse by emitting an ultrasonic wave into the ambient environment, such as a coronary artery, as explained in detail in the Proudian et al. patent. The chips 50-53 then switch to a receiving mode in order to detect echoes of the emitted ultrasonic waves resulting from reflections of the waves off the inner wall of a blood vessel, or similar small cavity, and impinging upon a transducer of the array 54. Upon detecting an ultrasonic wave impinging on it, a transducer bends or flexes. Because the transducer is a piezoelectric device, the flexing or bending is converted by the transducer into an electrical waveform (hereinafter an "echo waveform") that is detected by the chips 50-53 and amplified by a receiver amplifier 58 before being transmitted to the signal processor 38 and processed for viewing on the video display 40. The receiver amplifier 58 typically includes a chain of amplifiers (1), (2), (3) . . . (N) as illustrated for amplifying the low-level signal received from the piezoelectric elements 54.

After each element of the array 54 has been excited, however, it relaxes in accordance with a characteristic damped oscillation. The electrical signals generated by the damped oscillation of the transducer after it has been excited contribute to the echo waveform, and they are substantially greater than the electrical signals contributing to the waveforms that are generated by the flexing caused by acoustic echoes. The electrical signals generated by the damped oscillation are typically called "ringdown" signals, and they tend to saturate the output of the receiver amplifier 58.

FIG. 3b illustrates an echo waveform as it is amplified by the chain of amplifiers (1-N) of the receiver amplifier 58. The initial high amplitudes of the waveform result from the ringdown signal generated by one of the elements in the array of piezoelectric elements 54. By comparison to the amplitudes of the signals generated by reflected echoes, the amplitude of the ringdown signal is very large. As the echo waveform is further amplified to establish the waveform at a sufficient amplitude to be transmitted to the signal processor 38 (FIG. 3a), the ringdown signal in the waveform is clipped because some of the amplifiers begin to saturate at the higher amplitudes of the signal. For example, the output signal of amplifier (2) begins to saturate in response to the highest amplitudes of the ringdown signal, causing clipping of the echo waveform. Further amplification of the signal by amplifier (3) causes more of the signal to be clipped. As the ringdown signal continues to be amplified, the output of amplifier (N) has a significant portion of the ringdown signal clipped. Although large amplification of the echo waveform causes a significant portion of the ringdown signal to be clipped and thus any superimposed echo signals to be lost, this amplification is necessary in order to amplify the much smaller amplitudes of the echo signals to a magnitude enabling the entire waveform to be processed by the signal processor 38.

Figure 4:
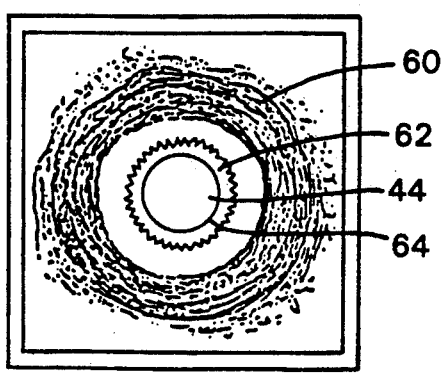
FIG. 4 is an exemplary cross-sectional image of a coronary artery generated by the imaging system of FIG. 1, where a near-field corona or artifact is generated around the imaging probe.

These ringdown signals generate an artifact around the surface of the imaging probe when the imaging data is processed and converted to a video image. FIG. 4 illustrates an exemplary video image that shows the vascular cross-section 60, the imaging probe 44 and the artifact 62, which looks something like a corona about the perimeter of the probe. Within the region of this corona, the imaging probe is blind since any echo information has been substantially lost due to the saturation of the receiver amplifier caused by the ringdown signal.

As discussed in the background of this application, the reference waveform is conventionally obtained by placing the imaging probe 44 in a tank of water large enough for collecting an echo-free signal—i.e., a reference signal. The reference waveform is composed of enough data points to fill a memory area of the imaging system dedicated for storing an entire echo waveform. For example, a typical reference waveform is composed of 2048 samples from an echo-free waveform, which corresponds to an echo-free environment of about seven (7) mm in radius.

As discussed in detail in the Proudian et al. patent, the level of noise in the echo waveforms is substantially reduced by generating multiple echo waveforms using the same element or elements of the array 54 and averaging the waveforms in order to get a single waveform for processing. Averaging the waveforms, however, does not remove the ringdown signal and any other characteristic noise signal that repeats with every generation of a new echo waveform. Averaging is effective in reducing noise levels because of the assumed randomness of the noise. Since the ringdown signal is not random, it is not effectively removed by averaging. Thus the need for a reference waveform that filters out repeatable noise patterns as opposed to random noise. Similar to the echo waveform, the reference waveform is the result of averaging multiple echo-free waveforms in order to ensure the reference waveforms includes only repeatable noise (e.g., the ringdown signal).

In accordance with one important aspect of the invention, the repeatable noise in an echo waveform is substantially the ringdown signal, which is effectively dissipated in the first 500–600 samples of the echo waveform, thereby allowing the reference waveform to be collected in a much smaller echo-free environment than previously thought possible. As suggested by the waveform of the output from amplifier (N) in FIG. 3b, the repeatable noise extends over a range of the echo waveform that begins at the origin of the waveform and ends after about one quarter ($\frac{1}{4}$) of the time period of the full waveform. Specifically, applicant has found that virtually all of the ringdown signal can be collected without an echo in one of the larger arteries that the probe assembly 44 is initially inserted into. Therefore, the reference signal can be collected in vivo and the need to place the probe into a water tank is eliminated. The time for the ringdown signal to substantially dissipate corresponds to the round trip travel time for an acoustic wave generated by one of the elements 54 and reflected from a surface approximately 0.7 mm in radial distance from the element. Because the ringdown signal can be substantially completely collected in the first 500–600 samples, the environment for collecting the reference signal need be only slightly greater than 1.45 mm in radius (i.e., 0.75 mm radius of the probe 44 plus 0.7 mm or more radial distance to nearest echo source).

Figure 5A:
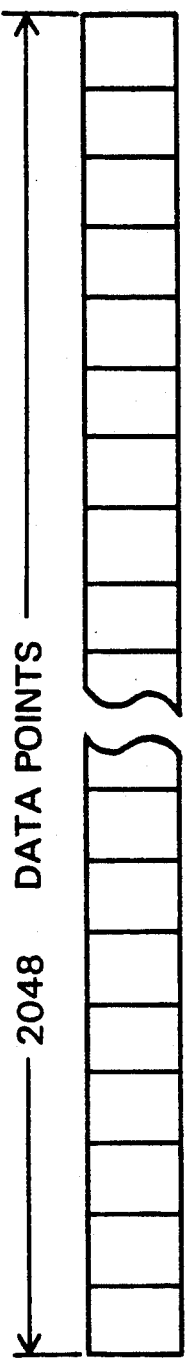
FIG. 5a illustrates a 2048-byte data buffer used in the prior art imaging system to store a reference waveform.
Figure 5B:
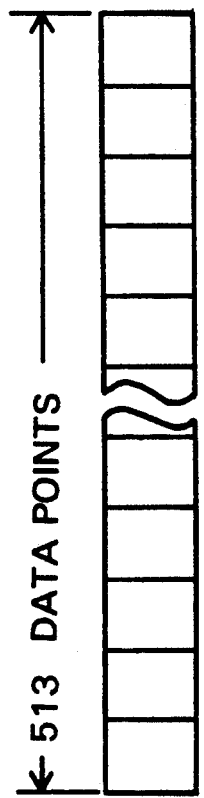
FIG. 5b illustrates a 513-byte data buffer used in the present invention to store a reference waveform.

The 500–600 data points in a normal data sampling (the conventional is 2048 samples) serve to store an adequate reference for removing the ringdown signal during processing of imaging signals. The use of 513 data points is exemplary of the illustrated embodiment. It may be that more or less are needed, depending on the sample rate and the characteristic rate of decay of the ringdown signal. The rate of decay of the ringdown signal depends on the precise design of the transducer 54 and probe 44. For the transducer and probe assembly of the Proudian et al. patent, 513 data samples have been found to be sufficient. FIGS. 5a and 5b illustrate the sample points of a conventional reference signal and those of a reference signal according to the invention, respectively.

Since the imaging probe is typically introduced into the vascular system of a patient at a large diameter section of a blood vessel, such as in the patient's leg, collection of data for the reference waveform can be performed without modifying the surgical procedure used in PTCA. Moreover, allowing the surgeon to record the reference waveform in vivo greatly simplifies the use of the imaging device and eliminates the risk of contaminating the probe 44 resulting from in vitro collection of the reference waveform. Additionally, in vivo collection of the reference waveform improves the accuracy of the image generated on the video display by providing improved acoustic impedance matching between reference and imaging signals, and eliminating temperature drift between reference and echo waveforms.

In keeping with the present invention, an imaging probe is introduced into a first area of a vascular system having a radius sufficiently large to enable a substantially complete ringdown signal to dissipate before an ultrasonic wave emitted in response to the excitation of the transducer element reflects off a first inner wall of the first area and impinges upon at least one element of the array 54. A reference waveform is collected in the first area of the vascular system, and then the imaging probe is further inserted to a second area, which is then imaged.

Figure 6:
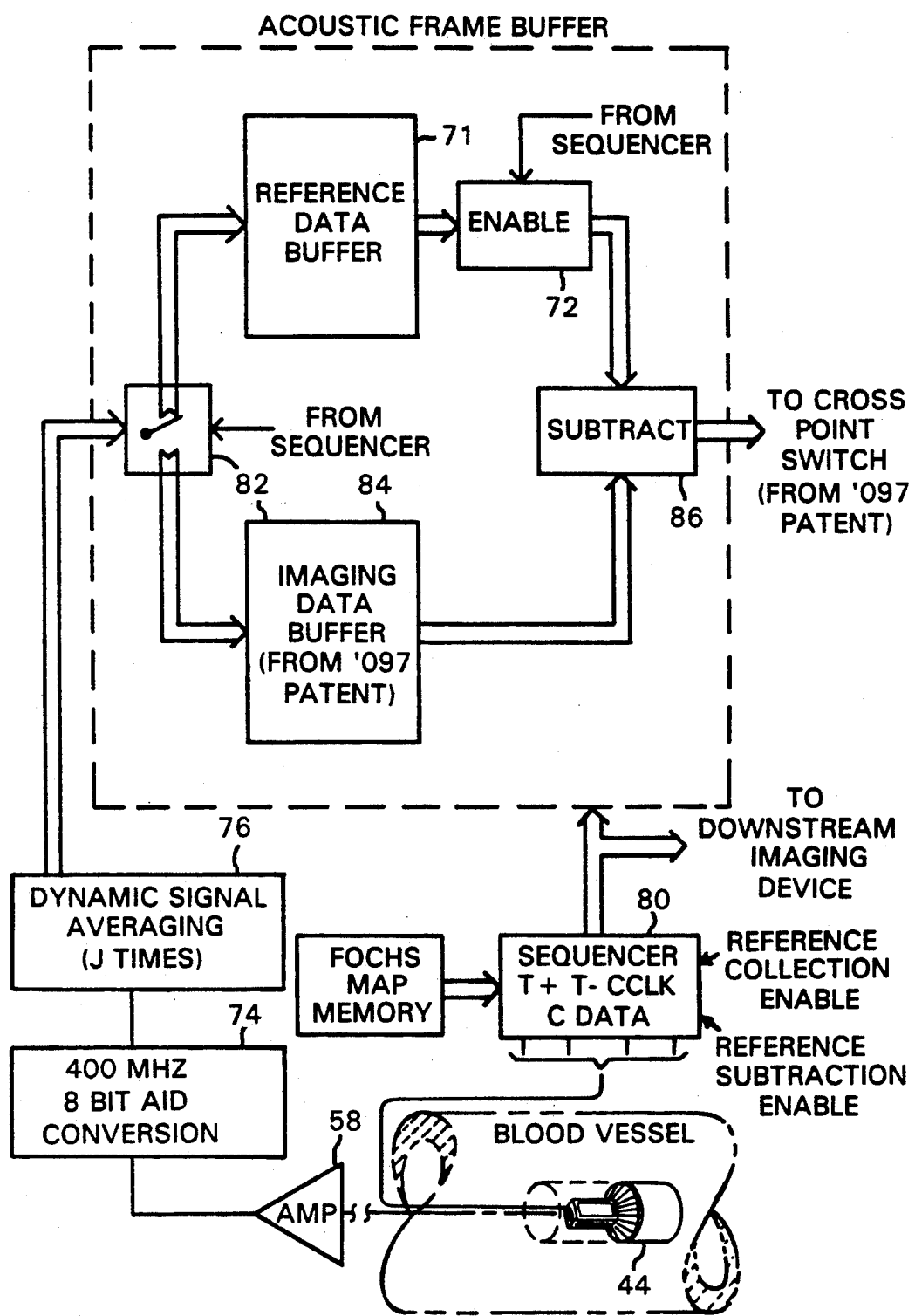
FIG. 6 is a schematic diagram of a signal processor according to the present invention for storing the 513-byte reference waveform and processing collected echo waveforms.

Referring to the signal processor of FIG. 6, it is substantially the same as that illustrated in FIG. 13a of the Proudian et al. patent, except the acoustic frame buffer 78 has been modified to include a buffer 70 for the reference waveforms. In the Proudian et al. patent, there are 64 transducer elements. In one embodiment described in detail in the Proudian et al. patent, each of the elements is excited individually in a predetermined sequence in order to create 64 echo waveforms. Therefore, in the embodiment illustrated herein, there are 64 reference waveforms stored in a reference data buffer 70 in FIG. 6. Since the signal processor illustrated in FIG. 6 is substantially similar to the processor whose function is explained in detail in the Proudian et al. patent, only the functioning of the processor necessary for an understanding of the gathering, storing and processing of the reference waveforms will be explained herein.

Although the reference waveforms in the illustrated embodiment are the averaged echo-free responses of each element taken alone, it will be appreciated by those skilled in the art of ultrasonic imaging that the collection of each echo waveform may employ the use of more than one transducer element. For example, elements 1, 2 and 3 of the 64 elements may be responsive to a first set of echoes in order to generate a first echo waveform. Elements 2, 3 and 4 may be responsive to a second set of echoes in order to generate a second echo waveform. The sequence of grouped elements continues in a pattern suggested by the foregoing two examples until 64 echo waveforms are collected. If such a sequence is employed to generate a set of echo waveforms, then the reference waveforms must be similarly collected. Therefore, in this example, each reference waveform would be the combined signal from three adjacent elements.

In practicing the present invention, echo waveforms from the imaging probe 44 are amplified by the receiver amplifier 58 and fed through an analog-to-digital converter 74 in order to produce 2048 sample points. The digitized data is then averaged by a signal averager 76. If the data is intended as a reference waveform, it is delivered to the reference data buffer 70. If the data is intended as imaging data, it is delivered to the imaging data buffer 84, which is identified as the entirety of the acoustic frame buffer in the Proudian et al. patent. In order to direct the digitized data to the proper data buffer, a switch 80 is responsive to a sequencer 80, which in turn is responsive to a "Reference Collection Enable" signal generated by the surgeon using the device in order to collect the reference data at the appropriate time. The sequencer 80 is discussed in greater detail in the Proudian et al. patent.

During the collection of data for the reference waveform, the probe 44 is positioned in the first area of the vascular system to be imaged and the "Reference Collection Enable" causes the sequencer 80 to enable the switch 82 to feed incoming digitized data to the reference data buffer 70. In the exemplary embodiment, each of the transducers is flexed in response to an electrical pulse in order to generate a reference waveform for each of the transducers, which is stored in the reference data buffer 70. In storing each of the reference waveforms, the first 513 sample bytes from the signal averages 76 are inserted into the data buffer. The remaining sample bytes for a full 2048 waveform are filled with zeros in order to match the 2048 byte of each echo waveform in the imaging data buffer.

After the reference waveforms have been collected and stored, the imaging probe 44 is further inserted to the second area of the vascular system that is to be imaged, and the surgeon causes the switch 82 to feed incoming data to an imaging data buffer 84 by sending a "Reference Subtraction Enable" signal to the sequencer 80. As discussed in detail in the Proudian patent ('097), each of the transducers is flexed to generate an ultrasonic wave that is reflected off the inner wall of the second area of the vascular system, and the reflected wave or echo impinges upon a transducer to produce an echo waveform, which is stored in the imaging data buffer 84.

From the imaging data buffer 84, the echo data is stripped of the ringdown signals by subtracting the echo data from the reference data on a point-by-point basis. The resulting imaging data are passed on to a cross-point switch (not shown) as explained in the Proudian et al. patent, where they are further processed and displayed on the video display 40. Unlike the procedure disclosed in the Proudian et al. patent, however, in the present invention the imaging data being passed to the cross-point switch from a subtraction means 86 (such as a conventional adder circuit) have a substantial portion of the ringdown signals removed from them. Furthermore, the entire procedure is performed within the vascular system that is being imaged.

Figure 7:
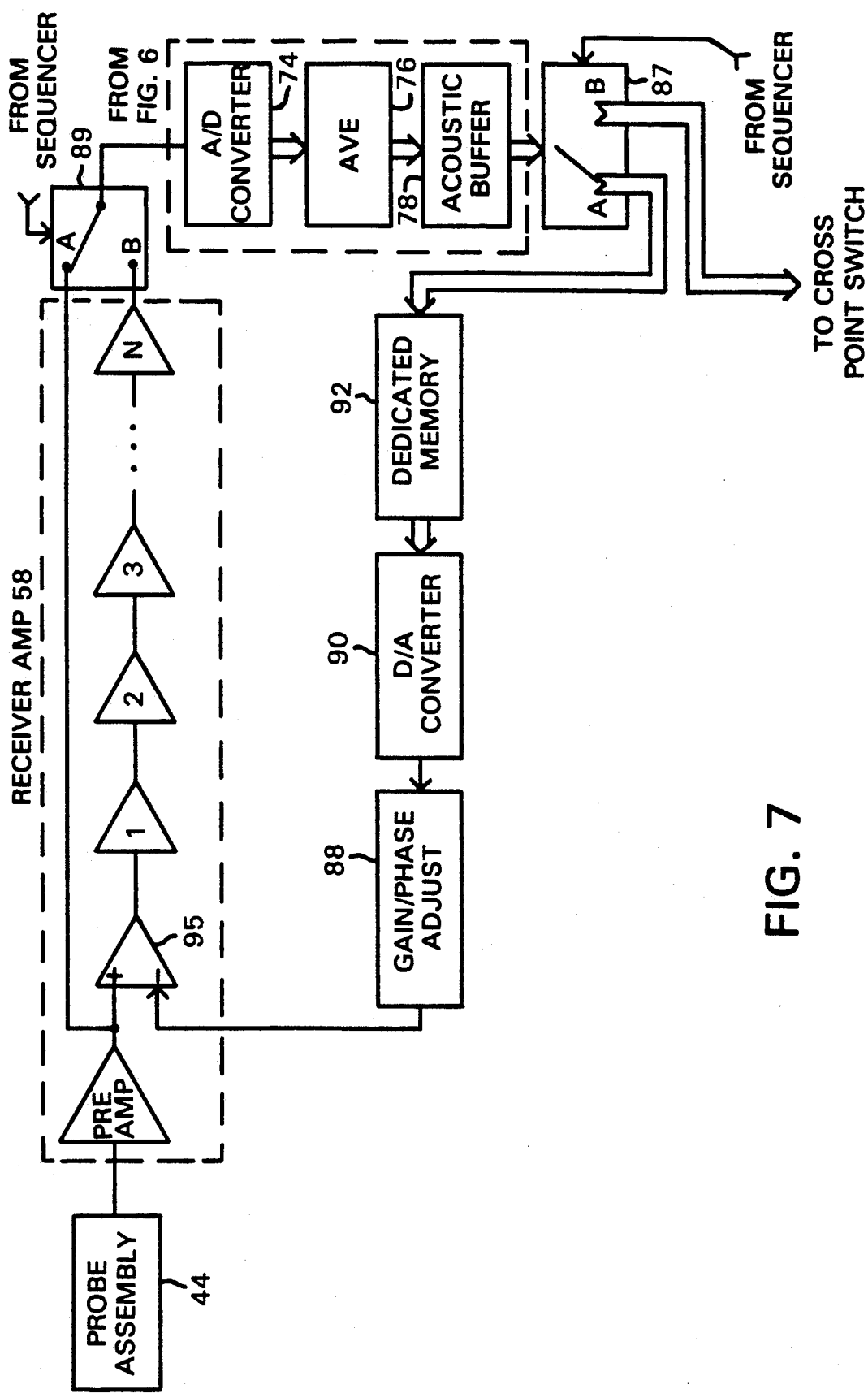
FIG. 7 is a schematic diagram of the signal processor of FIG. 6 modified in accordance with an alternative embodiment of the invention for the purpose of allowing the system to see in the near field previously occupied by the corona in FIG. 4, which provides an improved image.

In accordance with another important aspect of the present invention, FIG. 7 illustrates an improvement to the signal processor for reducing the corona 62 in the displayed image (FIG. 4) caused by saturation of the receiver amplifier 58. The improvement in FIG. 7 provides means for subtracting the ringdown signal from the echo waveform before it saturates the receiver amplifier 58.

In this alternative embodiment, the reference waveform is collected from the output of a pre-amplifier 93 instead of from the output of the amplifier (N). In this manner, the stored waveform is not clipped. The reference waveform is stored as a digital waveform that is delivered as a linear reference waveform to a differential amplifier 95 for the purpose of subtracting the ringdown signal from an echo waveform. Because the ringdown signal is removed before the chain of amplifiers (1)-(N) amplify the echo waveform, the echo data mixed in with the ringdown signal are not lost by the clipping of the signal.

As in the previous embodiment, the embodiment shown in FIG. 7 includes the imaging probe assembly 44, the receiver amplifier 58, the averager 76, the A/D converter 74, and the acoustic frame buffer 78. It further includes, however, switches 87 and 89, a gain/phase adjustment 88, a digital-to-analog converter 90, a dedicated memory 92, and a pre-amplifier 93. During the collection of reference data, the sequencer 80 (FIG. 6) moves the switches 87,89 to the "A" position and reference waveforms are passed through the A/D converter 74, the averager 76, and the frame buffer 78. The digitized reference waveforms are stored in the dedicated memory 92, which could be the reference data buffer 70 of FIG. 6.

When the probe assembly 44 is further inserted to the area of the vascular system to be imaged, the sequencer 80 moves the position of the switches 87,89 to "B" in response to a user-generated signal that the system is ready for imaging. As incoming echo waveforms are received by a positive input of the differential amplifier 95 in the receiver amplifier 58, corresponding reference waveforms stored in the dedicated memory 92 are passed through the D/A converter 90, the gain/phase adjust 88 and into a negative input of the differential amplifier 95. The gain/phase adjust 88 functions to ensure that the reference waveforms are precisely in phase with the incoming echo waveforms, thus causing the differential amplifier 95 to output an echo waveform substantially stripped of the ringdown signal. The outputted echo signal passes through the chain of amplifiers (1)-(N) in the receiver amplifier 58 in order to amplify the echo waveform to a sufficient magnitude for processing. The amplified echo waveforms pass through the switch 89, the A/D converter 74, the averager 76, the acoustic buffer 78, the switch 87, and onto the cross-point switch where the imaging waveform is processed and displayed as described in the Proudian et al. patent.

As a practical matter, the output of the differential amplifier 95 may contain some remnants of the ringdown signal that will be applied by the chain of amplifiers (1)–(N). Therefore, it may be desirable to store the amplified remnants as a second reference waveform in the acoustic frame buffer and subtract the second reference waveform from the stripped echo waveform in order to completely remove any artifacts from the resulting generated image.

From the foregoing, it will be appreciated that the present invention provides an improved method and apparatus for generating cross-sectional images of a small cavity such as a blood vessel. By reducing the number of sample points of a reference waveform relative to a full set of sample points used for collecting echo waveforms, applicant has found that the collection of the reference waveform can be done in the vascular system to be imaged, thereby eliminating the need to for in vitro generation of the reference waveform. The collection of the reference waveform in this manner has many advantages, not the least of which are the reduced risk of infection and the simplification of the imaging procedure. Furthermore, imaging can be further improved by subtracting the ringdown signal from the echo waveform before the signal is saturated by the receiver amplifier 58. In this manner, the corona 68 can be removed from the image and useful imaging information can be generated very close to the surface of the probe 44, thereby enabling the probe to image smaller arteries than previously possible.

I claim as my invention:

1. A method of imaging a cross section of a small cavity such as a coronary vessel using an imaging apparatus having a transducer, wherein the transducer flexes in response to a received electrical pulse so as to emit an ultrasonic wave into an ambient environment of the array within the small cavity, the method comprising the steps of:
   a. inserting the transducer into a first area of the cavity;
   b. delivering an electrical pulse to the transducer in order to generate an ultrasonic wave in the ambient environment of the array;
   c. detecting a ringdown signal generated by a damped oscillation of the transducer in response to its excitation by the electrical pulse;
   d. storing the ringdown signal as a reference waveform;
   e. inserting the transducer into a second area of the cavity having a diameter smaller than that of the first section;
   f. emitting ultrasonic waves into the second area by mechanically exciting the transducer in response to electrical pulses;
   g. generating an echo waveform in response to echoes of the emitted waves that are reflected off inner walls of the second section and impinge upon the transducer;
   h. subtracting the reference waveform from the echo waveform for the purpose of creating an imaging waveform stripped of the ringdown signal; and
   i. generating a visual image using a plurality of the imaging waveforms.

2. The method as set forth in claim 1 comprising the additional steps of repeatedly collecting ringdown signals for the transducer, averaging the collected ringdown signals and storing the average as the reference waveform.

3. The method as set forth in claim 1 comprising the additional steps of repeatedly generating echo waveforms from the transducer, averaging the echo waveforms and subtracting the reference waveform from the averaged echo waveform.

4. The method as set forth in claim 1 wherein a reference waveform is stored for each transducer in an array of transducers and each of the transducers produces an echo waveform.

5. The method as set forth in claim 1 wherein the transducer is one of a group of transducers that are excited in order to produce a single reference waveform and a single echo waveform.

6. The method as set forth in claim 1 wherein the ringdown signal stored as the reference waveform is substantially entirely linear.

7. The method as set forth in claim 6 wherein the reference and echo waveforms provide the two inputs of a differential amplifier and the output of the amplifier is the imaging waveform.

8. A method of imaging a cross section of a small cavity such as a coronary vessel, the method employing an imaging apparatus including a transducer, wherein the transducer flexes in response to a received electrical pulse so as to emit ultrasonic waves in an ambient environment of the transducer within the small cavity, the method comprising the steps of:
   a. positioning the transducer within a reference collection environment;
   b. emitting ultrasonic waves into the reference collection environment by exciting the transducer in response to an electrical pulse;
   c. detecting a ringdown signal generated by a damped oscillation of the transducer in response to the electrical pulse;
   d. storing the ringdown signal as a linear reference waveform;
   e. inserting the transducer into a small cavity to be imaged;
   f. emitting ultrasonic waves into the small cavity by exciting the transducer in response to an electrical pulse;
   g. detecting an echo waveform generated by echoes of the ultrasonic waves as they are reflected off surfaces of the small cavity and impinge upon the transducer;
   h. subtracting the reference waveform from the echo waveform so as to generate an imaging waveform;
   i. amplifying the imaging waveform such that the entire waveform remains linear; and
   j. processing the linear imaging waveform with other linear imaging waveforms in order to create a visual image of the small cavity.

9. The method of claim 8 wherein the reference collection environment is in an area of the small cavity.

10. An apparatus for imaging a cross section of a small cavity such as a coronary vessel, the apparatus including in combination:
    a probe having a transducer element;
    a source of an electrical pulse for exciting the transducer element to emit ultrasonic waves in an ambient environment of the transducer element within the small cavity;

a receiver for detecting electrical signals generated by mechanical oscillations of the transducer element after excitation of the transducer element by the electrical pulse;

a first buffer for storing the electrical signals as an echo waveform, comprising N bytes;

a second buffer for storing the electrical signals as a reference waveform, comprising M bytes of non-zero data, where $N>M$;

means for subtracting the reference waveform from the echo waveform in order to provide an imaging waveform stripped of any repeatable noise patterns; and an imaging device responsive to the imaging waveform for generating a visual image.

11. An apparatus for imaging a cross section of a small cavity such as a coronary vessel, the apparatus including in combination:

a prove having a transducer element;

a source of an electrical pulse for exciting the transducer element to emit ultrasonic waves in an ambient environment of the transducer element within the small cavity;

a receiver for detecting electrical signals generated by the mechanical flexing of the transducer element after excitation of the transducer element by the electrical pulse;

a first buffer for storing as a reference waveform electrical signals which are free of signals caused by echoes of the ultrasonic waves, where the reference waveform is substantially entirely linear;

means for subtracting the reference waveform from electrical signals that include signals caused by echoes of the ultrasonic waves in order to generate an echo waveform;

a second buffer for storing the echo waveform;

means responsive to the second buffer for generating visual images.

12. The apparatus of claim 11 wherein the means for subtracting the reference waveform from the electrical signals includes a differential amplifier wherein one input of the amplifier receives the reference waveform, a second input receives the electrical signals and an output provides the echo waveform.

* * * * *